United States Patent
Smith

[11] Patent Number: 5,228,435
[45] Date of Patent: * Jul. 20, 1993

[54] SINGLE PATIENT USE DISPOSABLE CARBON DIOXIDE ABSORBER

[76] Inventor: Charles A. Smith, 811 Starlite Dr., Louisville, Ky. 40207

[*] Notice: The portion of the term of this patent subsequent to Sep. 1, 2009 has been disclaimed.

[21] Appl. No.: 699,485
[22] Filed: May 13, 1991
[51] Int. Cl.$^5$ .............. A62B 7/10; A62B 23/02; A61M 16/00; F23D 11/00
[52] U.S. Cl. ............. 128/205.12; 128/204.17; 128/205.28; 128/203.26
[58] Field of Search ......... 128/201.25, 201.22–201.24, 128/201.26, 201.29, 205.27, 205.28, 205.29, 204.17, 202.22, 203.16, 203.17, 203.26, 203.27, 205.12, 205.13, 205.17, 205.23, 909, DIG. 24

[56] References Cited

U.S. PATENT DOCUMENTS

| | | | |
|---|---|---|---|
| 2,090,358 | 8/1937 | Reiter | 128/205.28 |
| 2,614,561 | 10/1952 | Fox | 128/205.28 |
| 2,675,885 | 4/1954 | Fox | 128/205.28 |
| 2,918,356 | 12/1959 | Hay | 128/205.28 |
| 3,240,567 | 3/1966 | Caparreli et al. | 128/205.28 |
| 3,566,867 | 3/1971 | Dryden | 128/205.28 |
| 3,707,965 | 1/1973 | Guzay | 128/205.28 |
| 3,713,440 | 1/1973 | Nicoles | 128/205.12 |
| 3,738,360 | 6/1973 | Dryden | 128/205.28 |
| 3,923,057 | 12/1975 | Chalon | 128/205.28 |
| 3,980,081 | 9/1976 | Cotabish et al. | 128/202.26 |
| 4,750,485 | 6/1988 | Bartos | 128/205.24 |
| 5,016,628 | 5/1991 | Lambert | 128/205.28 |
| 5,038,768 | 8/1991 | McGoff et al. | 128/205.28 |

FOREIGN PATENT DOCUMENTS

1424623 2/1976 United Kingdom ........... 128/204.17

Primary Examiner—Edgar S. Burr
Assistant Examiner—Kimberly L. Asher
Attorney, Agent, or Firm—Robert W. Fletcher

[57] ABSTRACT

An efficient, low cost, single-patient-use disposable carbon dioxide absorbing device which avoids use of any moving parts. A transparent flexible sac container having at least two openings for communication between the inside and outside of the container is described. The sac is included within a system for providing air to a patient by means of an airstream through a conduit. The sac includes granular, carbon dioxide absorbing material, an air inflow hose and an air outflow hose. The airstream enters the sac through the inflow hose and is dispersed into the granular material, which absorbs at least a major portion of the carbon dioxide in the airstream. The airstream then enters into the outflow hose and is provided to the patient, thus minimizing the deleterious effects of carbon dioxide in the breathing gas. The construction is of sturdy, lightweight materials minimize the effort and training which would normally be required for replacing a unit which has expended its carbon dioxide absorbing capability.

7 Claims, 2 Drawing Sheets

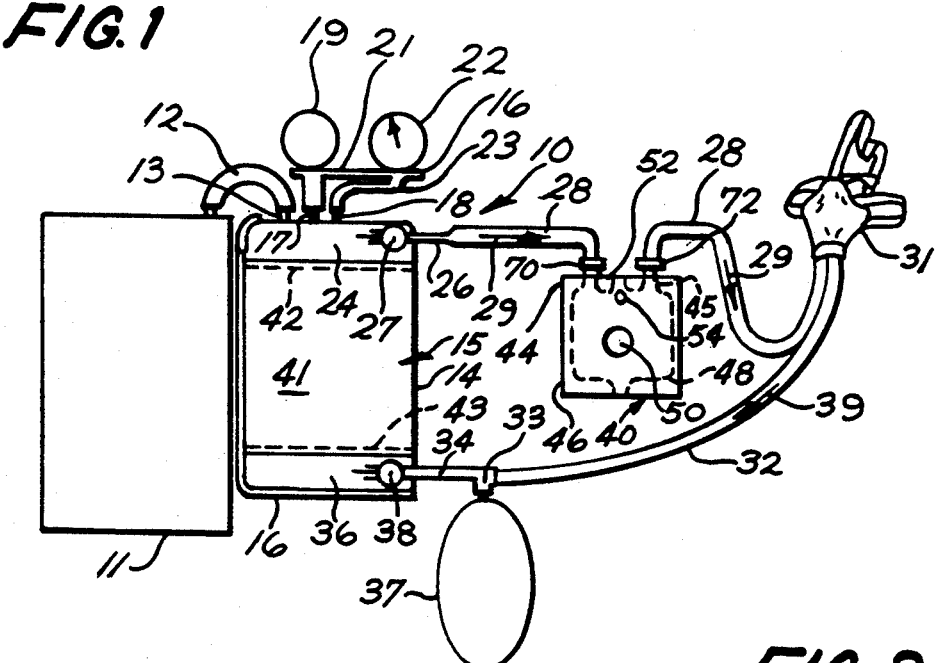
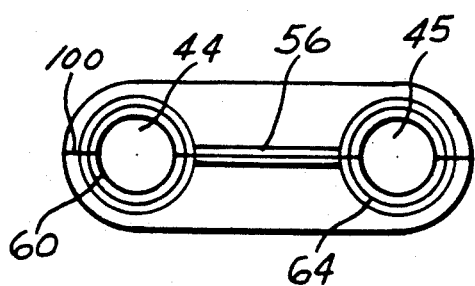
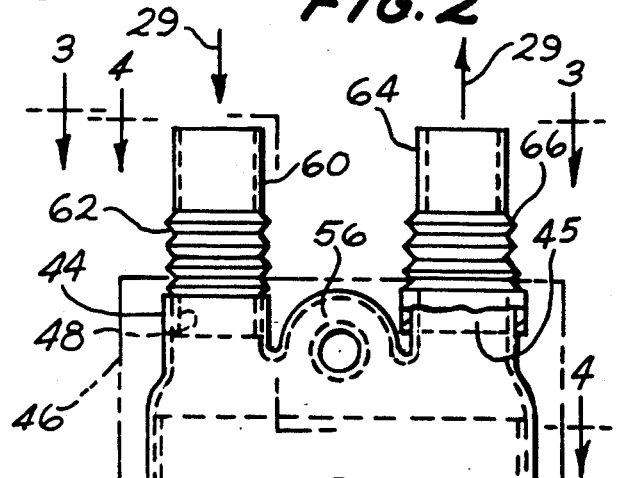
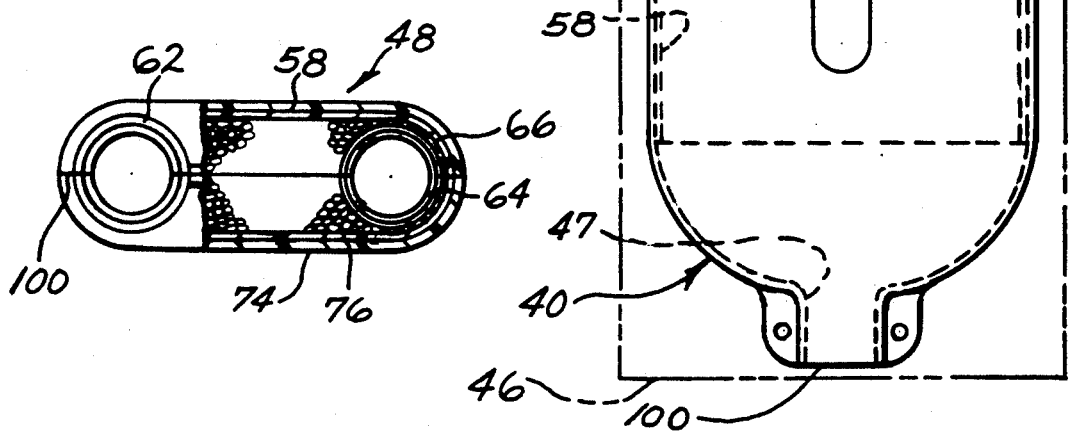

SINGLE PATIENT USE DISPOSABLE CARBON DIOXIDE ABSORBER

BACKGROUND OF THE INVENTION

The present invention relates to carbon dioxide absorption devices used in breathing assistance systems and more particularly to recirculatory aided respiration systems for surgical or other medical applications, usually involving anesthesia.

In the use of recirculating breathing assistance systems, particularly with patients who are experiencing breathing difficulty because of trauma, surgical procedures, anesthesia, or other reasons, it is generally desirable to provide heated and humidified air to the patient. Warm, humidified air prevents "drying out" of the mucociliary tissues of the patient's respiratory system, and reduces patient heat loss that may result from evaporation of water vapor from the lungs. It is also desirable that the air provided to the patient be relatively free of any contamination, especially of contamination which may result from previous use of the system by another patient.

Complicated, hazardous, and relatively expensive apparatus has often been employed to condition the air supplied to a patient in a recirculatory aided respiration system. Where such system is in use for a surgery or other operating room procedures, anesthesia gases or other conditioning agents are often introduced into the stream of air inhaled by the patient. Also, any recirculation system requires the removal of carbon dioxide from the air exhaled by the patient.

Such prior art systems for warming and humidifying air supplied to a patient often require the use of water reservoirs, humidifiers, and complicated delivery systems including complex electrical/electronic controls. Those systems may require complex hose connections and knowledge of the control systems; they may also require a significant amount of space in the operating room. Setup of these prior art systems can be quite complicated, and the systems may require substantial capital outlay as well as costly supplies. In such previous applications, the use of heaters and humidifiers is prevalent in order to provide proper conditioning for the air and entrained gases supplied to the patient.

SUMMARY OF THE INVENTION

By proper utilization of the heat typically generated by the reaction of carbon dioxide with a granular absorbent material, such as soda lime, and by effective insulation, the typically expensive and often troublesome arrangements of a heated humidifier, water supply, reservoir, hose connection system, electronic monitoring and control, bulky mounting apparatus, and other generally complicated arrangements as employed in the prior art can be much simplified or eliminated. The carbon dioxide removal, heating, and humidifying functions can also be isolated from an associated anesthesia machine to prevent cross contamination between patients. The capability of a single-use disposable device to warm, humidify and filter the air stream recirculated to the patient, and to provide great flexibility and convenience to medical personnel utilizing such a device is highly advantageous. One device providing all of these features and advantages is the subject matter of a pending U.S. patent application Ser. No. 07/590,947, filed on Oct. 1, 1990 by the inventor of the present invention. This invention is another device that achieves the same fundamental objects in a different manner.

The present invention relates to the heating and humidification of air to be supplied to a patient which eliminates electrical/electronic humidifiers, heaters, and other related apparatus, previously listed and generally required by previous procedures, to properly condition the air before it returns to the patient. In general, a device within the scope of the present invention absorbs carbon dioxide from recirculated air mixed with anesthesia gases, and simultaneously warms and humidifies the air. The device can also include means for filtering out dust, which is prevalent in most carbon dioxide removal devices. Nevertheless, the devices of the invention are simple and inexpensive enough so that the complete carbon dioxide absorbing unit can be disposable after only a single patient use.

The single patient use device of the present invention does not require the flow control valves normally included in conventional carbon dioxide absorption devices. Rather, any of the devices of the present invention may be utilized together with the elements of a conventional carbon dioxide absorber, such as flow control valves, air bar, hoses, etc., to provide a carbon dioxide absorption capability for the "life" of the soda lime or other $CO_2$ absorption material, after which disposal of the single use unit of the present invention and replacement by a new disposable unit ensues. An important feature of the present invention is that the only portion of the breathing assistance system which is discarded is that portion which ceases to be operational, i.e., the carbon dioxide absorbing material itself. Moreover, the device provides all of the features of a convention carbon dioxide absorber with the additional feature that replacement of the stale $CO_2$ granules is performed quickly and easily with the disconnection and reconnection of only two hoses.

The disposable device according to the present invention is thermally self regulating; as more air is circulated, the air heating and humidification increases. That is the amount of heat generated in the exothermic reaction used for $CO_2$ absorption correspondingly increases because of the increased quantity of carbon dioxide produced by the patient. Insulation disposed around the device, the hoses, and other elements of the system reduces heat loss.

Accordingly, the invention relates to a single-patient-use disposable device for removing carbon dioxide from, and increasing the moisture content and temperature of, air delivered to a patient connected in a recirculatory aided respiration system including an anesthesia machine having an inlet flow control valve and an outlet flow control valve, the system including an exhalation conduit through which a stream of air exhaled by the patient flows to the inlet valve of the anesthesia machine, and an inhalation conduit through which a stream of air from the outlet valve of the anesthesia machines flows to be inhaled by the patient. The device comprises a sealed, transparent, flexible sac having an inlet opening and an outlet opening, and a mass of granular soda lime or other carbon dioxide absorption material that reacts with carbon dioxide in gas passing through the material to remove the carbon dioxide from the gas while increasing the temperature and the moisture content of the gas, in the sac. An inlet tube sealed into the inlet opening of the sac, the inlet tube having a connection end located outside of the sac and connectable to the inhalation valve of the absorber mechanism, the inlet tube further having an air flow end extending into the sac, the air flow end of the inlet tube including at least one air opening through which air flows from the inlet tube into the carbon dioxide absorption material. An outlet tube sealed into the outlet opening of the sac, the outlet tube having a connection end located outside of the sac and connectable to the one conduit, the outlet tube further having an air flow end extending into the sac, the air flow end of the outlet tube including at least one air opening which may be a microfilter for removal of bacteria and virus and dust through which air flows from the carbon dioxide absorption material into the outlet tube. The device has no flow control valves.

BRIEF DESCRIPTION OF THE DRAWINGS

FIG. 1 is a schematic diagram of a recirculatory aided respiration system, constituting an anesthesia system, in which the present invention is incorporated;

FIG. 2 is an elevation view, on an enlarged scale, of a single-use disposable carbon dioxide absorption device that comprises one embodiment of the invention;

FIG. 3 is a detail sectional view taken approximately as indicated by line 3—3 in FIG. 2;

FIG. 4 is a detail sectional view taken approximately as indicated by line 4—4 in FIG. 2;

DESCRIPTION OF THE PREFERRED EMBODIMENTS

Figure 5:
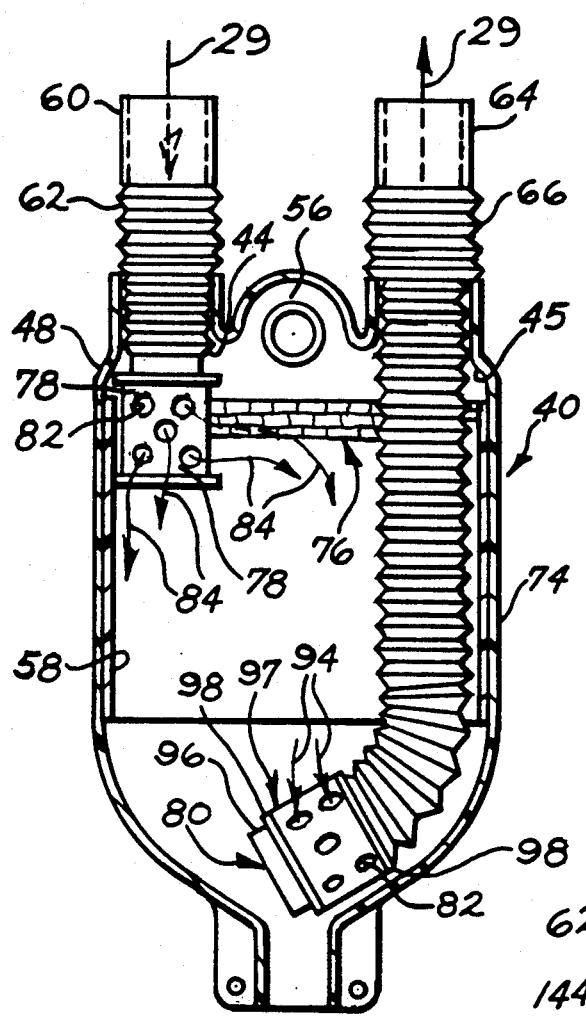
FIG. 5 is a sectional elevation view of the carbon dioxide absorber device of FIGS. 2-4.

The recirculatory aided respiration system 10 illustrated in FIG. 1, which is actually an anesthesia system, includes a conventional anesthesia or "gas" machine 11. Machine 11 is utilized to provide a desired mix of anesthetic gases through a hose 12 to a fitting 13 that is a part of the casing 14 of a device 15 that would normally serve system 10 as a carbon dioxide absorber, but that does not serve that function in system 10. Device 15 may be mounted upon anesthesia machine 11 by suitable means such as a bracket 16, as shown schematically in FIG. 1. There are two other tubular fittings 17 and 18 at the top of the housing or canister 14 of device 15. A pressure relief valve 19 is connected by a hose 21 to fitting 17 and a manometer or other pressure indicator 22 is connected by a hose 23 to fitting 18.

The three fittings 13, 17 and 18 each communicate with an outlet chamber 24 located, in the illustrated system, in the top of device 15. Device 15 has a unidirectional outlet flow control valve 27 mounted in chamber 24 to permit only outward flow of air from chamber 24 through an outlet port 26 into an inhalation hose or conduit 28, sometimes referred to as a rebreathing hose. A face mask 31 included in system 10 is connected to conduit 28 so that a patient wearing the mask can receive air, mixed with anesthetic gases, flowing to the patient in the direction indicted by arrows 29.

System 10 includes another conduit or hose 32, sometimes referred to as an exhalation or exhaust conduit. Hose 32 extends from the patient's mask 31 to a T-fitting 33 that is connected to an inlet port 34 for device 15. Port 34 is in turned connected, by a unidirectional valve 38, to an inlet chamber 36 in the bottom of device 15. A rebreathing bag 37 is also connected to the T-fitting 33. The flow of air through conduit 32 and into the inlet chamber 36 of device 15 is in the direction indicted by arrow 39.

Device 15 includes a central chamber 41 separated from the outlet chamber 24 by a wall 42 and separated from the inlet chamber 36 by another transverse wall 43. Wall 42 is provided with a plurality of apertures (not shown) to permit the flow of air from chamber 41 to chamber 24. Similarly, wall 43 includes a multiplicity of apertures (not shown) to allow the flow of air from inlet chamber 36 into central chamber 41. In a conventional system the central chamber 41 would be filled with an absorption mass of a granular carbon dioxide absorption material; the $CO_2$ absorption material typically comprises granular soda lime, though some other propriety carbon dioxide absorption materials are occasionally used. In system 10, however, the chamber 41 of device 15 is empty.

As thus far described, system 10 would be quite conventional if the canister, device 15, were filled with soda lime or some other $CO_2$ absorber material. When the patient wearing mask 31 exhales, the exhaled air passes through conduit 39 to the inlet port 34 that leads into the inlet chamber 36 of the carbon dioxide absorption device 15 through the inlet flow control, check valve 38. A part of the air exhaled by the patient may pass into the rebreathing bag 37.

When the patient wearing mask 31 inhales, air is drawn from the outlet chamber 24 of device 15 through the outlet flow control valve 27 and outlet port 26 into the inhalation hose or conduit 28. Additional air and anesthetic gases may be introduced into chamber 24 from machine 11 to pass to the patient. The pressure in the system is held to an acceptable level by the relief valve 19. Other controls may be provided, usually in the anesthesia machine 11.

A major problem with recirculatory aided respiration systems, such as the anesthesia system 10, is that the movement of air must take place through the carbon dioxide absorption device that they utilize. For example, device 15 would present such a problem if its chamber 41 were filled with soda lime, which leads to the entrainment of dust and even larger granules of soda lime or other carbon dioxide absorption material into the air stream. This action is decidedly undesirable, particularly with respect to possible effects upon the patient wearing mask 31.

Another problem of major proportions is that device 15, in the conventional system, ought to be replaced for each new patient to avoid inter-patient spread of contamination. Device 15 may be treated as a single use device for this purpose, but it is really too expensive and complex for such use. Consequently, hospital and other service personnel are inclined to sterilize and recharge the device 15 with carbon dioxide absorption material and use it again. This is a poor practice. Sterilization is difficult and adds to the expense of system operation. It may be ineffective, to the decided detriment of the next patient. And the service personnel may simply neglect to sterilize or even re-charge device 15, with potentially disastrous results.

To minimize and eliminate these problems, the recirculatory breathing assistance system 10 is modified to include a simple, inexpensive, single-patient-use, truly disposable device 40 for removing carbon dioxide from the air delivered to a patient wearing mask 31. This device 40 is shown interposed in series in the inhalation conduit 28, and that is the preferred arrangement, but device 40 could also be connected in series with the exhalation conduit 32 of the system.

The $CO_2$ absorption receptable or device 40 includes an air inlet 44 and an air outlet 45, through which the air enters and exits while passing through the recirculation circuit. Shown in FIG. 1, and in phantom in FIG. 2, device 40 includes a styrofoam or polyfoam bag 46, which fits snugly around, and acts as a pouch for the container 48, shown in FIG. 2, and in phantom in FIG. 1. Container 48 is also referred to as a sac 48, and comprises a sac made from two transparent flexible walls which are sealed together, the seal providing openings 44, 45 and 47 for communication between the outside and inside of the sac. The bag 46 insulates to the container 48, the requirement for which will be explained below. The bag 46 also includes a viewing aperture 50 which provides a view into the container 48 to a viewer who may wish to inspect the contents of the container 48.

The bag 46 further provides a pair of coupling holes 52, one on either side of the walls of bag 46. Each coupling hole 52 lines up with an aperture 54 in the container 48. When the apertures 52, 54 are lined up, a hook (not shown) may be passed through all of the apertures and thus permitting the device 40 to be temporarily coupled and suspended from a hook (not shown). Suspension of the device 40 is desirable so that it does not weigh down the conduit 28. Avoidance of weighing down of the conduit is desirable because any weight on conduit 28 pulls at mask 31 and causes discomfort to the patient.

Referring now to FIGS. 2, 3 and 4, the container 48 is shown in greater detail. Coupling hole 52 is shown as being formed by a loop 56 of the bag 46. The loop 56 is disposed between the arms formed by air inlet 44 and air outlet 45. FIG. 4 shows in cross section an optional reflective metal foil 58 disposed on the inside of bag 48. If used, reflective foil 58 will tend to minimize radiant heat loss from the device 40, thus maintaining heat within the device 40.

Air inlet 44 includes a female joining member 60 attached to the air inlet 44 by a corrugated hose section 62, which may be a conventional 22 mm. hose. Similarly, air outlet 45 includes a male joining member 64, attached to the air outlet 45 by a section of corrugated hose 66, which may also be a conventional 22 mm. hose. Corrugated hoses 62, 66 provide flexibility to the connection of the joining members 60, 64 to the conduit 28.

As will be shown below, it is important that the air inlet 44 and air outlet 45 be differentiated. Accordingly, disposing a female joining member 60 at air inlet 44 and a male joining member 64 at air outlet 45 ensures only proper connection will be made of the device 40 into the conduit 28 of system 10. For example, to connect a device 40 into a system 10, a conduit hose 28 includes a connection (not shown) within its length of a male member within a female member, shown in FIG. 1 as 70 and 72, respectively. The connection of members 70, 72 provides a continuous passageway for an airstream through conduit 28. That connection is first broken, and the male member 70 is inserted into female joining member 60 and the female member 72 is disposed over male joining member 64, thus once again completing the air flow circuit through conduit 28. A connection of the separate sections of conduit 28 to each other may thus be temporarily broken for insertion of device 40 without creating stress to the breathing cycle of the patient.

Male and female joining members 70, 72 are thus associated with each section of conduit 28. Each of these can only be fitted onto the joining members 60, 64 in one way, thus ensuring that the connection of the device is made properly. Such a system also provides flexibility in that use of the device 40 in system 10 may be omitted if air purification is not desirable. It is not required that a female joining member be associated with the air inlet 44 and a male joining member be associated with the air outlet 45. The opposite relationship may be used; the only important consideration being the consistency of the connections to ensure correct operation of the device 40, as will be explained below.

Referring now to FIGS. 4 and 5, detail sectional views of the device 40 are shown, partially illustrating the passively operating parts of the device 40. Similar elements shown in greater detail or in their full configuration will be identified by identical numerals between the respective Figures. FIG. 4 is a detail sectional view taken along line 4—4 of FIG. 3, and showing in cross section the wall 74 of container 48, reflective foil 58, and corrugated hoses 62, 66. Disposed between the corrugated hoses 64 and 66 are granules 76 of an absorbent material which absorbs carbon dioxide from the airstream flowing through the device 40. The $CO_2$ absorbent material may be soda lime or the like as is described above.

Referring now to FIG. 5, a partial sectional elevational view of the carbon dioxide absorber device 40 is illustrated, showing both ends of each of the corrugated hoses 62, 66. Female joining member 60 defines one end of corrugated hose 62 and provides an air inlet 44 into the device 40. At the other end of hose 62 there is disposed an air stream inflow opening 78. Similarly, the male joining member 64 defines one end of the corrugated hose 66 which provides for an air outlet 45 from the device 40. An airstream outflow opening 80 defines the other end of corrugated hose 66.

As shown in FIG. 5, corrugated hose 66 extends much further into the space bounded by the container 48, and the airstream outflow opening 80 is disposed as far as possible from the airstream inflow opening 78. Opening 78 includes inflow apertures 82 for egress of the airstream into the space bounded by container 48. Arrows 84 indicate the flow of air from the inflow apertures 82 into and through the granular material 76. As will be explained below with relation to FIG. 6, inflow apertures 82 are covered by a nonwoven fiber material 86 held on to the opening 78 by elastic bands 88. The construction of nonwoven fiber material 96 is set forth in greater detail in U.S. patent application No. 07/674,682, filed on Mar. 21, 1991, having common inventorship with the present invention. The disclosure of that application is incorporated herein by reference.

Similarly, outflow opening 80 has outflow apertures 82 which permit the outflow of the airstream from the granular material 76 into the opening 80 as indicated by arrows 94. An identical nonwoven fiber material 96 covers outflow opening 80 and is held in place by means of rubber bands 98.

As the arrows 86 and 96 indicate, the airstream flowing out of apertures 82 must flow into and between the granular material 76 and must flow from the container 48 and into corrugated hose 66 through outflow apertures 92. As will be explained below, container 48 is a hermetically sealed enclosure in which the inlet 44 and outlet 45 are sealed to the corrugated hoses 62 and 66 as is the edge 100 of the container 48 and the terminus 102 of the container opposite the air inlet 44 and air outlet 45. The airstream path, as shown by arrows 84 and 94, requires that the air pass through as much as possible of the granular material 76 in container 48. This expends as much as possible of the carbon dioxide absorbent capability of the granular material 76 because most of the material 76 comes into contact with the passing airstream.

Granular material 76 is comprised of large granules of soda lime or the like. Soda lime changes color after its $CO_2$ absorbent capacity has been expended. Thus the viewing aperture 50 in bag 46, discussed with regard to FIG. 1 above, provides a view of the granules 76 through a clear wall portion of the container 48, for an indication of a color change. If the color change is sufficient to indicate that the granules no longer absorb a sufficient amount of $CO_2$, then the complete container 48 may be removed from the system 10 by disconnecting male and female joining members 60 and 64 and replacing the container 48 with a new container containing fresh $CO_2$ absorbing material 76.

Figure 6:
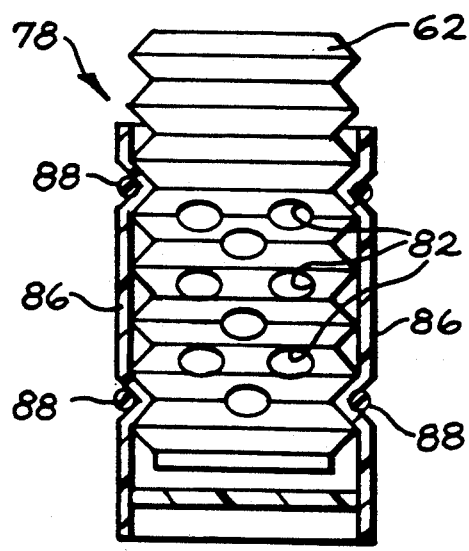
FIG. 6 is a detail view, on an enlarged scale, partly in cross-section, of a portion of the device of FIGS. 2-5.

Referring now to FIG. 6, a termination, as defined by inflow openings 78, 80 of either of the two corrugated hoses 62, 66, is illustrated. For the sake of consistency with FIG. 5, a partial cross-sectional view of inflow opening 78 is shown. Inflow apertures 82 are disposed within the termination of corrugated hose 62. The apertures 82 are preferably about one-half inch in diameter and are disposed in the wall of hose 62. Apertures 82 can be punched out by appropriate means. The hose 62 itself requires a cap 102 at its terminal to block air flow.

To avoid dust infiltration from the granular material 76 into the airstream of hose 62, an absorbent material dust filter 86 is shown in cross section. Filter 86 covers the entire section of hose 62 in which the apertures 82 are disposed and is effective in filtering all dust particles from granular material 76 from entering the hose 62. To retain the dust filter 86 on the section of corrugated hose 62, elastic bands 88, made of an elastomer material, are snapped over the filter 86 and settle within on of the troughs of the corrugated hose 62. The trough formed by the corrugations of hose 62 retains the elastic band 88 and the dust filter 86 in place. No air flows through cap 102, and thus there is no need for the dust filter 86 to cover the terminal of hose 62. Although only hose 62 has been discussed and illustrated in detail by FIG. 6, similar treatment of the outflow opening 80 is provided for the termination of corrugated hose 66.

In the embodiment of FIGS. 2 and 5, a bottom section 47 of the device 40 is sealed, and the outflow of the airstream is through an opening 45 disposed near the inflow opening 44. During manufacture of the device 40, once the corrugated hoses 62 and 66 are in place, the granular material 76 is injected into the container 48 and the bottom end 47 of the container is sealed by an appropriate method such as heat-sealing. The configuration shown in FIG. 5 requires that the terminations of the corrugated hoses 62, 66 be as far apart as possible from each other, and thus requires that corrugated hose 66 to be of greater length than that of hose 62.

Figure 7:
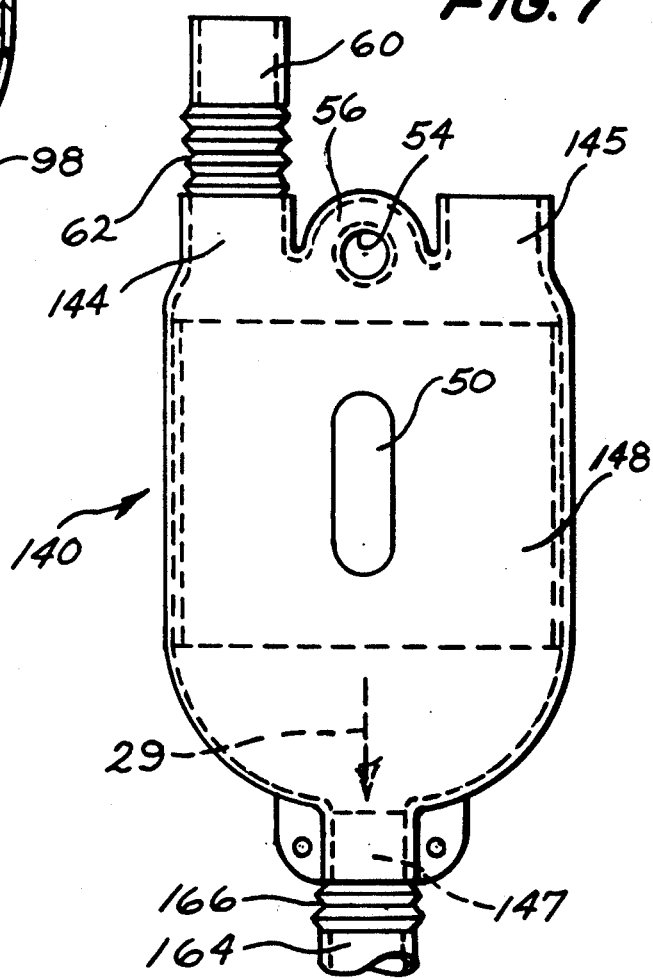
FIG. 7 is an elevation view, similar to FIG. 2 of another embodiment of the invention.

FIG. 7 illustrates an alternative embodiment of the inventive device showing an alternative disposition of inflow and outflow hoses. As is shown in the configuration of device 140, a container 148 is illustrated which is similar to the container 48. Female joining member 60, corrugated hose 62 and the rest of the inflow opening (not shown) are identical to that described above with regard to the container 48 which is illustrated in FIG. 5.

A major difference in the configuration of FIG. 7 is evident, however, in that the male joining member 164 is disposed within the bottom 147 of container 148. Corrugated hose 166 is disposed within the container 148 and sealed to the bottom 147 much as is the corrugated hose 62. During manufacture, the granular material (not shown in FIG. 7) is inserted into the container 148 through opening 145. After container 148 is filled with granular absorbent material, opening 145 is heat sealed.

The configuration of FIG. 7 thus does not require the excess length of hose which is shown in the embodiment of FIG. 5, thus keeping with the objective of decreasing costs in the manufacture of the devices 40 and 140, and is in accordance with the development of a single use disposable product.

Although the invention is shown and described in the embodiments discussed above, other alternatives will become apparent to a person of ordinary skill in the art, once an understanding is had of the invention. Accordingly, the described embodiments are only descriptive and not limiting, and the scope of the invention is to be defined by the following claims.

I claim:

1. In a recirculating aided respiration system for patients a single-patient use readily insertable device connectable in flow-through relationship in said respiration system, said system including an anesthesia machine, an exhalation conduit through which a stream of air exhaled by the patient flows to the anesthesia machine, and an inhalation conduit through which a stream of air from the anesthesia machine flows to be inhaled by the patient, the device comprising:

in combination an inner and outer container defining an enclosure means each container having a common inlet opening and a common outlet opening;

a mass of granular soda lime or other carbon dioxide absorption material that reacts with carbon dioxide in the air exhaled by the patient passing through the material to remove the carbon dioxide therefrom while increasing the temperature and the moisture content of the air;

the inner of said two containers further characterized in that it surrounds and retains said mass of granular soda lime and the outer of said containers being spaced from said inner container thereby defining an insulating space therebetween disposed adjacent and inside the wall of the outer container;

an inlet tube in flow communication with the inlet opening of the containers, the inlet tube having a connection end located outside of the enclosure means and connectable to either the inhalation or exhalation conduit; and an outlet tube in flow communication with the outlet opening of the containers, the outlet tube having a connection end located outside of the enclosure means and connectable to the other of the inhalation or exhalation conduits, the outlet tube further having an air flow end through which air flows from the carbon dioxide absorption material.

2. The single-patient-use device according to claim 1 in which each of the inlet and outlet tubes is a corrugated, flexible plastic tube.

3. The single-patient-use disposable carbon dioxide absorption device according to claim 1 in which the air flow end of the outlet tube is covered by a dust filter to preclude migration of dust or granules from the enclosure means into the outlet tube.

4. The single-patient-use disposable carbon dioxide absorption device according to claim 1 in which the air flow ends of both the inlet and outlet tubes are covered by dust filters to preclude migration of dust, granules, or other like contaminants into or out of the enclosure means.

5. The single-patient-use disposable carbon dioxide absorption device of claim 1 wherein said container includes flexible holding means for supporting said container in operating position while connected as a part of said recirculatory aided respiration system.

6. The device of claim 1 wherein said inner container includes a heat reflective film.

7. The device of claim 1 wherein both the inner and outer containers are transparent.

* * * * *